United States Patent [19]

Oliver et al.

[11] 4,221,125
[45] Sep. 9, 1980

[54] APPARATUS AND METHOD FOR DETECTING THE PRESENCE OF A SUBSTANCE ON A LIQUID SURFACE

[75] Inventors: John N. Oliver, Danville, N.H.; Louis M. Sandler, North Reading, Mass.

[73] Assignee: Emhart Industries, Inc., Indianapolis, Ind.

[21] Appl. No.: 19,147

[22] Filed: Mar. 9, 1979

[51] Int. Cl.³ .................... G01N 25/18; G01N 33/18
[52] U.S. Cl. ............................. 73/61.1 R; 73/362 SC
[58] Field of Search .......... 73/61.1 R, 359 A, 362 SC

[56] References Cited

U.S. PATENT DOCUMENTS

| | | | |
|---|---|---|---|
| 3,576,472 | 4/1971 | Marshall . | |
| 3,712,116 | 1/1973 | Andre | 73/61.1 R X |
| 4,047,435 | 9/1977 | Keith | 73/362 SC |
| 4,116,045 | 9/1978 | Potter | 73/61.1 R X |

FOREIGN PATENT DOCUMENTS

| | | | |
|---|---|---|---|
| 2745232 | 4/1979 | Fed. Rep. of Germany | 73/61.1 R |
| 565221 | 7/1977 | U.S.S.R. | 73/362 SC |

Primary Examiner—Gerald Goldberg
Assistant Examiner—Joseph W. Roskos
Attorney, Agent, or Firm—Robert F. Meyer; David W. Gomes

[57] ABSTRACT

An apparatus for detecting the presence of a substance on a liquid surface utilizes a single semiconductor sensing element having a thermal resistance which is related to the thermal conductivity of the environment surrounding it. A control logic sequentially and periodically samples and stores ambient temperatures of the environment surrounding the sensing element, subsequently heats the sensing element, samples and stores peak temperatures of the sensing element resulting from the heating, and finally differentiates between the ambient temperatures and peak temperatures to detect any change in the difference therebetween.

23 Claims, 5 Drawing Figures

APPARATUS AND METHOD FOR DETECTING THE PRESENCE OF A SUBSTANCE ON A LIQUID SURFACE

The present invention relates to an apparatus for detecting the presence of a substance on a liquid surface. For example, the present invention is adaptable for detecting oil and other hydrocarbon spills on a water surface whereby oil pollution of water may be detected and controlled.

Generally speaking, the apparatus of the present invention includes a single semiconductor sensing element having a thermal resistance which is related to the thermal conductivity of the environment in proximity to the sensing element. A control logic periodically and sequentially samples and stores measured ambient temperatures of the environment surrounding the sensing element, subsequently heats the sensing element, samples and stores measured peak temperatures of the sensing element, and differentiates between the ambient temperatures and peak temperatures to detect a change in difference therebetween indicative of the presence of a substance. Importantly, the apparatus and detection method of the present invention do not rely upon a constant ambient temperature of the environment surrounding the sensing element for accuracy of operation.

The apparatus and method of the present invention utilize the general principle of providing at least one sensing element adapted to be in contact with a liquid wherein an electrical characteristic of the sensing element is responsive to the thermal conductivity of the liquid in proximity thereto. If a substance other than the liquid contacts the sensing element, the thermal conductivity will be different from the conductivity when only the liquid surrounds the sensing element thereby causing a change in the thermal conductivity of the environment surrounding the sensing element and a change in the electrical characteristic of the sensing element.

Heretofore, numerous systems and schemes have been developed for sensing the presence or absence of a material, whether it be a liquid or some other substance, of which U.S. Pat. Nos. 3,576,472; 3,712,116; and 4,116,045 are exemplary. Essentially, each of the inventions disclosed in these patents employs at least two sensing elements each integrated into a bridge circuit where one of the sensing elements provides a reference and a change in the electrical characteristic of the other sensing element due to the presence or absence of a substance results in an unbalancing of the bridge circuit. In general, the electrical characteristic measured in these prior devices and in the present invention is the thermal resistance of the sensing element where typically the resistance of the sensing element increases when the thermal conductivity of the proximal environment decreases. Each of the inventions disclosed in the patents referenced above employ a thermistor or a tungsten filament as a sensing element.

In U.S. Pat. No. 3,712,116 two thermistors are utilized in a bridge circuit. One of the thermistors is situated in a reference liquid and the other is situated in the liquid to be monitored. When a change in thermal conductivity occurs in the liquid being monitored the bridge circuit becomes unbalanced thereby causing an output signal indicative of the presence or absence of a foreign substance.

In both U.S. Pat. Nos. 3,576,472 and 4,116,045, two thermistors or tungsten filaments respectively are utilized in bridge circuits; however in each of the inventions disclosed therein at least one of the two sensing elements is heated. In U.S. Pat. No. 3,576,472 the reference sensing element remains substantially unheated and senses an ambient temperature of its surrounding environment for comparison to electrical characteristics of the heated thermistor. A change in the characteristics of the two thermistors above or below a fixed reference due to an increase or decrease of the thermal conductivity of the proximal environment to the heated thermistor is detected. As disclosed in these prior references, heating of the monitoring thermistor is done periodically in both cases. In U.S. Pat. No. 4,116,045 the reference sensing element and the monitoring sensing element are simultaneously heated. The rate of change in the electrical characteristics of the sensing elements are subsequently compared to detect the presence or absence of the substance. In U.S. Pat. No. 3,576,472 the change in the characteristics of the two thermistors is detected during the heating period; whereas, in U.S. Pat. No. 4,116,045 the change in the electrical characteristics of the sensing elements is compared and detected after heating i.e. during a cooling period.

As evidenced by the three patents referenced hereinabove, prior detection systems have required two or more sensing elements and a bridge circuit to detect the presence or absence of a substance on a liquid surface. Furthermore, the reference sensing element being incapable of occupying the same location as the monitoring sensing element cannot provide a true reference with respect to the liquid in proximity to the monitoring sensing element because the reference sensing element may be either situated in an area of the liquid which is remote to the monitoring sensing element or in an entirely different liquid or environment altogether.

One aspect of the present invention is the use of a single semiconductor sensing element, which in the preferred embodiment is a diode, to serve as both the reference and monitoring sensing element and the storing of sensed temperatures to be differentiated. Another aspect is the employment of a control logic for sequentially and periodically sampling and storing measured ambient temperatures of the proximal environment of the sensing element, for subsequently heating the sensing element, for sampling and storing measured peak temperatures of the sensing element resulting from the heating thereof, and for differentiating between the measured peak temperatures and the measured ambient temperatures to determine a change in such difference.

The control logic includes means for sequencing and timing the various operations associated with the apparatus, thereby allowing the use of a single sensing element; means for sampling and storing measured ambient temperatures and measured peak temperatures, and means for differentiating between the ambient temperatures and peak temperatures.

A method in accordance with the present invention includes the steps of storing ambient temperatures sensed by a sensing element situated at a liquid surface, subsequently heating the sensing element by applying heating power thereto for a predetermined period of time; storing peak temperatures of the sensing element resulting from the heating thereof, differentiating between the stored ambient temperatures and stored peak temperatures, and detecting a change in the difference therebetween.

Other features and advantages of the present invention will be apparent from the following detailed description of a preferred embodiment thereof, which description should be considered in conjunction with the accompanying drawings in which.

Figure 1:
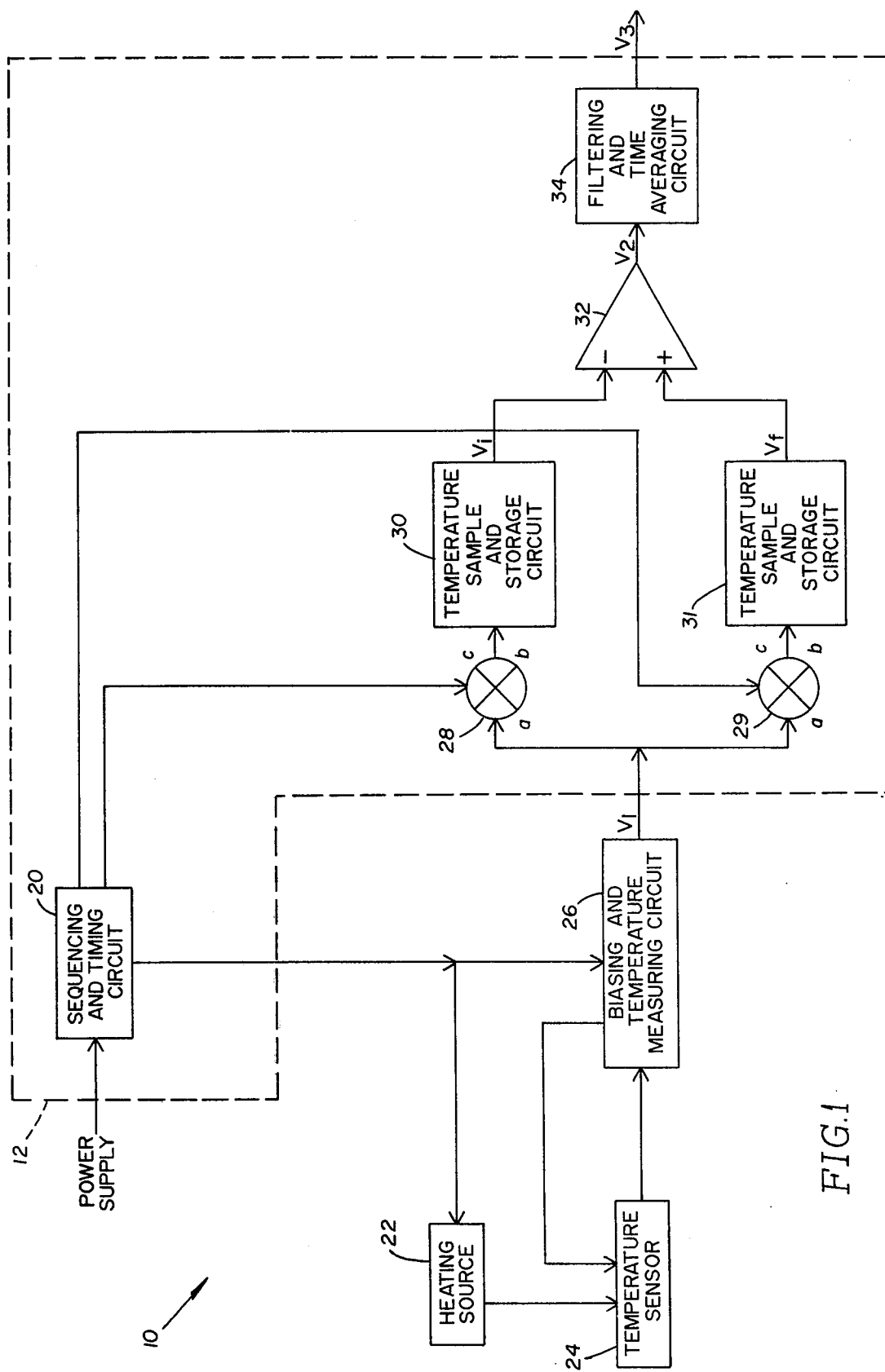
FIG. 1 is a schematic functional block diagram of an apparatus for detecting the presence or absence of a substance on a liquid surface to be described as an illustrative embodiment of the present invention.

Referring to FIG. 1, an apparatus 10 for detecting the presence or absence of a substance on a liquid surface (not shown) generally includes the following elements; preferred embodiments of which will be described in more detail hereinafter. A control logic 12 sequentially and periodically samples and stores ambient temperatures measured by a temperature measuring circuit 26 in proximity to a temperature sensor 24, energizes a heating source 22 which applies constant heating power to the temperature sensor 24 for a predetermined period of time, samples and stores peak temperatures of the temperature sensor 24 resulting from the heating thereof which are again measured by the temperature measuring circuit 26, differentiates between the stored ambient temperatures and the stored peak temperatures, and time averages such differences in temperatures whereby a significant change in the difference between the stored temperatures is detectable as indicative of the presence or absence of a substance. The temperature measuring circuit 26 preferably will also include circuitry for biasing the temperature sensor 24 employed in the present invention in a manner to be described later.

Control logic 12 is responsive to a conventional power supply and includes the control strategy for operation of the apparatus 10. It will be understood by these skilled in the art that control logic 12 may comprise a single large scale integrated (LSI) circuit such as a microprocessor or microcomputer which is programmed to accomplish the various functions described hereinabove. As illustrated in FIG. 1, one embodiment of control logic 12 includes a sequencing and timing circuit 20 having three outputs for sequentially and periodically activating and deactiviating the various functions of the apparatus 10, two bilateral switching devices 28 and 29 each of which transmits an analog signal $V_1$ (voltages) indicative of a temperature measured by the temperature measuring circuit 26 asynchronously with respect to the other in response to the various states of two of the outputs of sequencing and timing circuit 20, a temperature sample and storage circuit 30 for sampling and storing the analog signals $V_i$ (voltages) indicative of measured ambient temperature in proximity to the temperature sensor 24 in response to a closed state of bilateral switching device 28, a temperature sample and storage circuit 31 for sampling and storing analog signals $V_f$ (voltages) indicative of measured peak temperatures of temperature sensor 24 to heating from heating source 22 in response to a closed state of bilateral switching device 29, a difference amplifier 32 for comparing and differentiating signals $V_1$ and $V_f$ to provide a difference signal $V_2$, and a filtering and time averaging circuit 34 for assuring that a change in the signal $V_2$ is not merely a spurious signal misrepresentative of the presence or absence of a substance on the liquid surface. Accordingly, a signal $V_3$ (voltages) is provided as an output of control logic 12 representing the differences between ambient temperatures measured in proximity to the temperature sensor 24 ($V_i$) and measured peak temperatures of the sensor 24 due to heating by heating source 22 ($V_f$) whereby a change in the filtered and time averaged difference signal $V_3$ may be detected by any conventional detection circuitry.

In general, heating source 22, temperature probe 24, bilateral switching devices 28 and 29, temperature sample and storage circuits 30 and 31, and difference amplifier 32 include conventional electrical circuitry and therefore require only a brief discussion thereof.

Heating source 22 may be any conventional heating current source which in response to an appropriate signal from control logic 12 (an output of sequencing and timing circuit 20) is periodically energized to provide constant heating current (power) to the temperature sensor 24. In the preferred embodiment of the invention, temperature sensor 24 is a zener diode which is biased by biasing and temperature measuring circuit 26 to operate in the reverse direction while being heated and biased to operate in the forward direction during temperature sensing. By reverse biasing the zener diode when heating, the higher zener diode voltage in the reverse direction allows considerably more heating power to be applied thereto causing the sensor 24 to operate at higher temperatures thereby improving its accuracy. It will be understood that while the zener diode is a preferred temperature sensor 24, an ordinary diode may be utilized to produce satisfactory results and in fact various other p-n junction temperature sensing devices e.g. a transistor may be substituted for the zener diode without departing from the spirit or essence of the present invention.

While the functions associated with bilateral switching devices 28 and 29, with temperature sample and storage circuits 30 and 31, and with difference amplifier 32 may each be performed by a totally integrated control logic 12, such as a microcromputer, for the embodiment illustrated in FIG. 1 each comprises an individual conventional circuit. Bilateral switching devices 28 and 29 are transmission gates having the capability of controlling or implementing logical signals. The transmission gates are closed and an analog signal $V_1$ is transmitted between terminals a and b in response to a logical one (1) signal at the digital input c. As long as a logical zero (0) signal is applied to the digital input c, the transmission gate remains open. Temperature sample and storage circuits 30 and 31 may be any conventional sample and hold circuit. For example, a CA 3140 Bi Mos operational amplifier manufactured by RCA may be applied in a conventional manner to provide a sample and hold circuit for performing the functions of temperature sample and storage circuits 30 and 31. Difference or operational amplifier 32 may be of the type manufactured by National Semiconductor Corporation in a dual integrated circuit package identified as LM 747. The primary requirement of the difference amplifier 32 is that it have the capability of differentiating between voltages $V_i$ and $V_f$ to provide an output voltage signal $V_2$ indicative of differences between measured ambient temperatures ($V_i$) and measured peak temperatures ($V_f$) of the temperature sensor 24.

A more detailed description of the operation of the sequencing and timing circuit 20, the biasing and temperature measuring circuit 26 and the filtering and time averaging circuit 34 will be provided later; however, in general the apparatus 10 as shown in FIG. 1 operates as follows. A DC voltage is applied to control logic 12 and more particularly sequencing and timing circuit 20 by a power supply wherein the DC voltage is converted into a plurality of waveforms representing various time periods (See FIG. 3). These waveforms in conjunction with associated logic circuitry cause the three outputs of sequencing and timing circuit 20 to periodically change logical states. Initially, a logical (1) one is applied to bilateral switching device 28 while the other two outputs of sequencing and timing circuit 20 have appropriate logical states to maintain heating source 22 and bilateral switching device 29 off or open. Accordingly, temperature sensor 24 (zener diode) is biased in a forward direction by biasing and temperature measuring circuit 26 and the ambient temperature of the proximal environment to temperature sensor 24 is measured and sampled and stored by biasing and temperature measuring circuit 26 and temperature sample and storage circuit 30 respectively. As shown in FIG. 1, voltage $V_1$ provided by circuit 26 is initially voltage $V_i$ representative of the measured ambient temperature which is sampled and stored by sample and storage circuit 30. Thereafter, both bilateral switching devices 28 and 29 are opened in response to logical (0) zero outputs of circuit 20 and an output signal of circuit 20 having an appropriate logical state is provided to heating source 22 and to circuit 26 whereby temperature sensor 24 is biased in the reverse direction and heating source 22 is energized to provide a heating current to temperature sensor 24. Temperature sensor 24 is heated for a period of time predetermined by the sequencing and timing circuit 20 during which the temperature sensor 24 reaches a peak temperature. This peak temperature of the temperature sensor 24 resulting from the heating thereof depends upon the thermal conductivity of the proximal environment of the temperature sensor 24 because the thermal resistance of the sensor 24 i.e. the sensor's 24 ability to dissipate heat to the environment, is inversely related to changes in the thermal conductivity of the surrounding environment. Accordingly, as the thermal conductivity of the environment decreases (with the presence of a hydrocarbon) the thermal resistance of the sensor 24 increases and therefore the peak temperature of the sensor 24 increases.

Conversely, as the thermal conductivity of the environment increases (e.g. the sensor 24 becomes totally immersed in the liquid) the thermal resistance of the sensor 24 decreases and therefore the peak temperature of the sensor 24 decreases. Importantly, it should therefore be noted that the apparatus is adaptable to detect the presence of a substance on a liquid surface; the absence of a substance on the liquid surface or some other condition such as the total submersion of the sensor 24 in the liquid in response to a change in the difference between measured ambient temperatures and measured peak temperatures where the change may be either an increase or decrease in the peak temperatures.

The heating source 22 is then degenergized in response to an appropriate logical state of an output signal of circuit 20 and immediately thereafter or almost instanteously therewith a logical (1) one signal is applied to bilateral switching device 29. Switching device 29 is therefore closed, temperature sensor 24 is again biased in a forward direction, the peak temperature of the sensor 24 due to the heating is measured before the sensor 24 has cooled, and the measured peak temperature is sampled and stored by temperature sample and storage circuit 31. Again, as shown in FIG. 1, voltage $V_1$ provided by circuit 26 is at this period of time in the operation of apparatus 10 equivalent to voltage $V_f$ representative of the peak temperature of sensor 24 which has been sampled and stored by circuit 31.

Difference amplifier 32 then differentiates between $V_i$ and $V_f$ to provide a voltage difference $V_2$ indicative of the difference between the measured ambient temperature ($V_i$) of the proximal environment to the sensor 24 and the peak temperature ($V_f$) of the sensor 24 due to heating and related to the thermal conductivity of the proximal environment. A change in the difference voltage $V_2$ is therefore detectable as the absence or presence of a substance which has a thermal conductivity which is different (less or greater) than that of the liquid/air interface in which the sensor 24 is situated or detectable as the complete submersion of the sensor 24 in the liquid having a thermal conductivity which is less than that of the liquid/air interface.

In order to assure that a change in the difference voltage $V_2$ is filtered and time averaged by a circuit 34 so that the output voltage $V_3$ of control logic 12 provides an accurate indication of any change in the difference between voltages $V_i$ and $V_f$.

Figure 2:
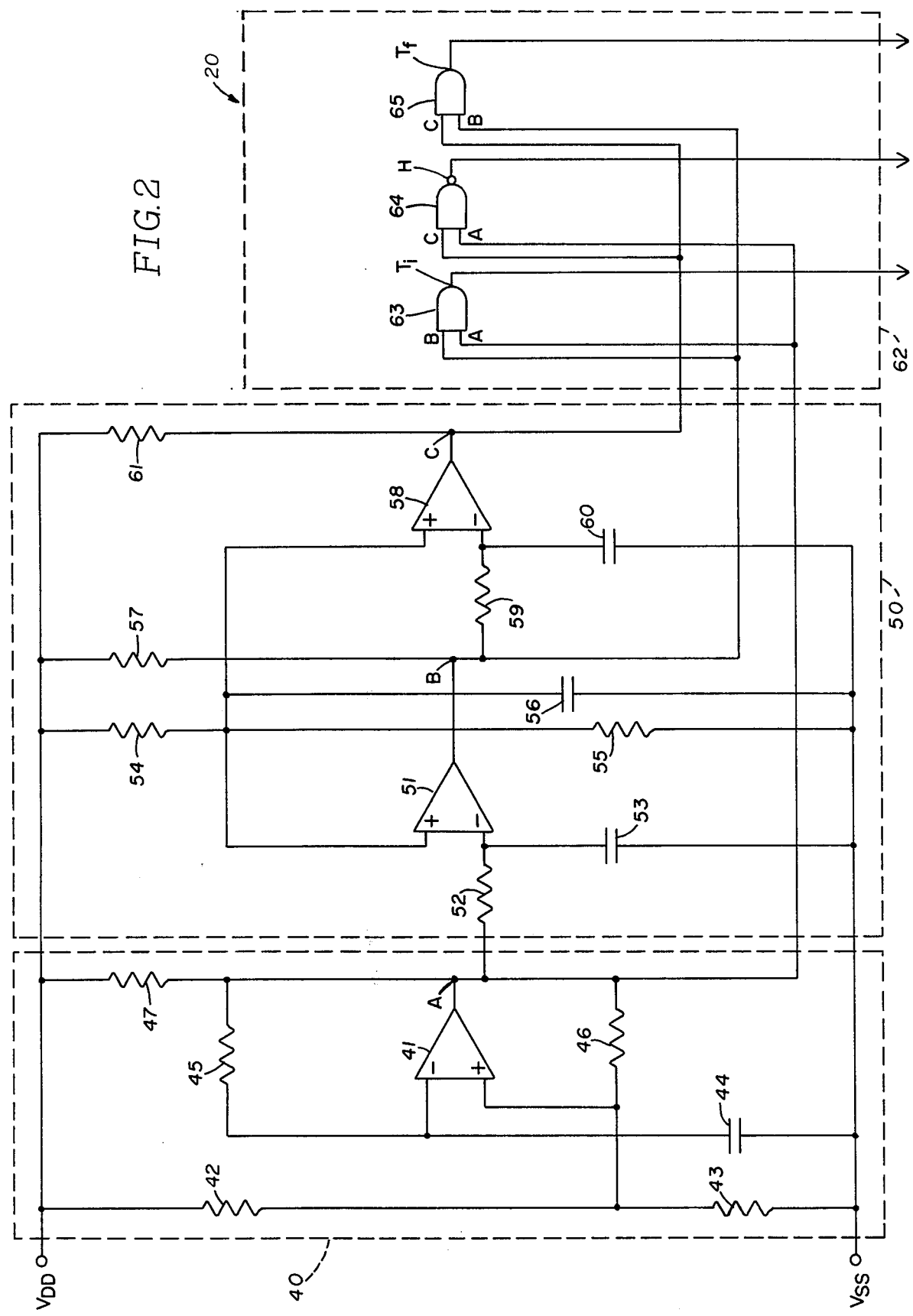
FIG. 2 is a schematic circuit diagram of an embodiment of a functional section of the apparatus shown in FIG. 1.
Figure 3:
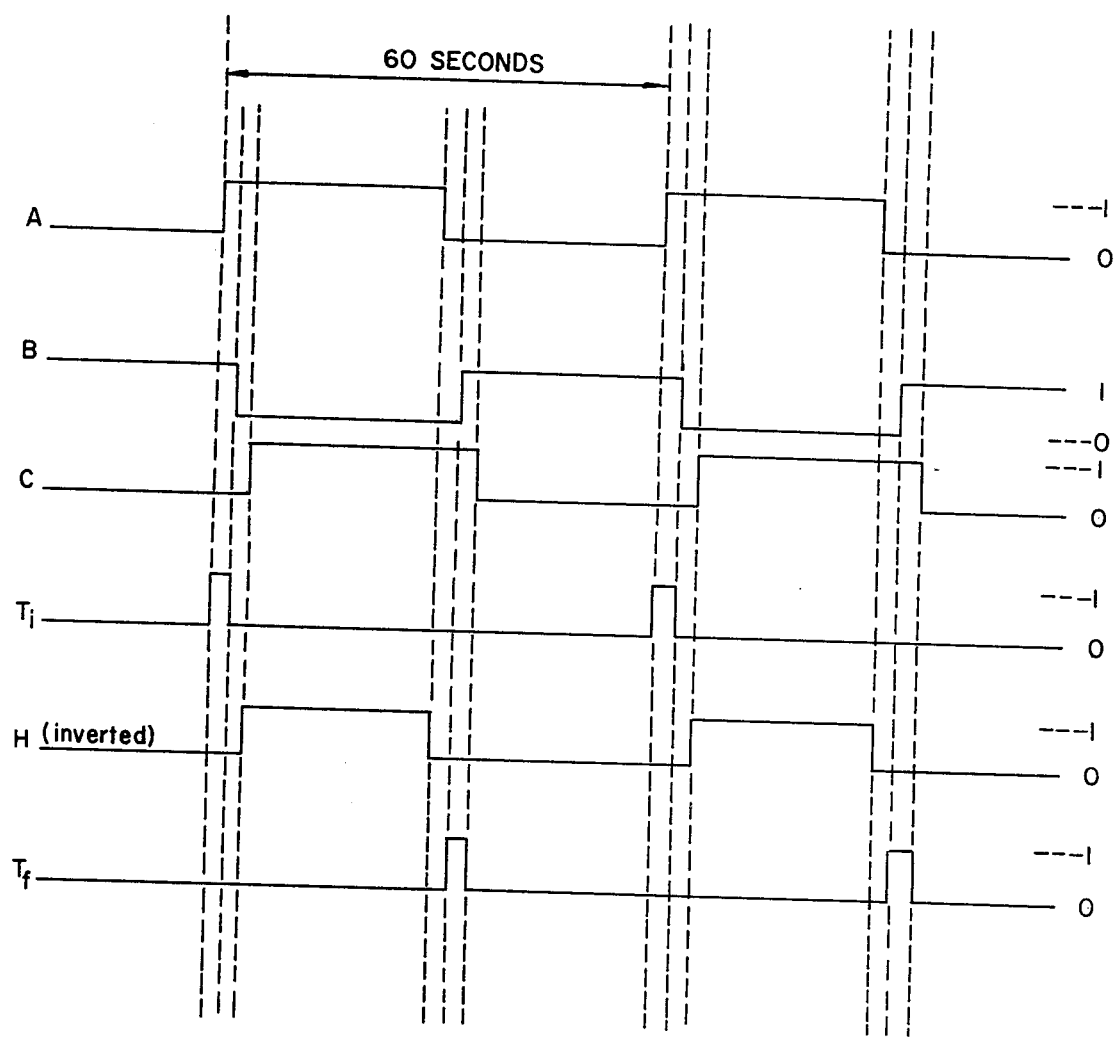
FIG. 3 is a comparison of waveforms taken at selected locations in the schematic circuit shown in FIG. 2.

An embodiment of sequencing and timing circuit 20 is shown in FIG. 2 and associated therewith various waveforms taken at selected locations in the schematic diagram of FIG. 2 are compared in FIG. 3 in order to assist in understanding the operation of sequencing and timing circuit 20.

Referring to FIGS. 2 and 3, a multivibrator circuit 40 functions as a squarewave oscillator providing an electrical pulse every 60 seconds at junction A, as shown in FIG. 3, thereby establishing a time base for the activation and deactivation of the various functions associated with the apparatus 10. A conventional voltage comparator 41 such as the LM 2901 series manufactured by National Semiconductor Corporation in combination with various resistors 42, 43, 45, 46 and 47 and a capacitor 44 are electrically coupled in a conventional manner to form a squarewave oscillator. As is well known in the art, the frequency of the pulses provided a junction A will depend upon the component values of the various resistors 42, 43, 45, 46 and 47 and capacitor 44 comprising the squarewave oscillator.

The electrical pulse produced at junction A is delayed for relative short periods of time and inverted by a time delay and inverting circuit 50 such that the waveform provided at junction B (See FIG. 3) is inverted and delayed in comparison to the waveform at junction A and the wave the RC time constant associated with comparator 51. Comparator 58 in combination with resistors 54, 55 and 59 and capacitors 56 and 60 are also electrically coupled in a conventional manner to form another squarewave oscillator which again delays and inverts the input signal (the waveform at junction B) providing a waveform at junction C as shown in FIG. 3. The delay of the waveform at junction B will also be determined by the value of the RC time constant associated with comparator 58.

A sequencing circuit 62 includes three logic gates 63, 64, 65 which in response to the waveforms provided at junctions A, B, and C of the squarewave generators establish a control strategy for the activation and deactivation of the various functions associated with the apparatus 10. It should be noted that the gates 63, 64, and 65 may be inverting as well as non-inverting depending upon the polarities associated with the remaining circuity of apparatus 10. As shown in FIG. 2, a two-input AND gate 63 is responsive to the pulses provided at junctions A and B. During the period of time that the pulses at junctions A and B are both a logical one (1) the output $T_i$ of gate 63 is logical one (1) as shown in FIG. 3. At all other times the output $T_i$ of gate 63 is logical zero (0). The output $T_i$ of gate 63 is applied to transmission gate 28 (FIG. 1) so that the voltage $V_i$ representative of the ambient temperature of the temperature sensor 24 is sampled and stored in response to a logical one (1) state of output $T_i$.

A two-input NAND gate 64 is responsive to the pulses provided at junctions A and C. During the period of time that the pulses at junctions A and C are both logical one (1) the output H of gate 64 is logical zero (0). At all other times the output H of gate 64 is logical one (1). As shown by the inverted waveform in FIG. 3, an AND gate could be used as a substitute for the NAND gate where the signal required to activate the heating source 22 must be a logical one (1) rather than logical zero (0). The output H of gate 64 determines the length of time during which heating power will be applied to temperature sensor 24. In the preferred embodiment of apparatus 10, the temperature sensor 24 is heated periodically for periods of substantially 30 seconds in response to the output H of gate 64.

Another two-input AND gate 65 is responsive to the pulses provided at junctions B and C. During the period of time that the pulses at junctions B and C are both a logical one (1) the output $T_f$ of gate 65 is logical one (1) as shown in FIG. 3. At all other times the output $T_f$ of gate 65 is logical zero (0). The output $T_f$ of gate 65 is applied to transmission gate 29 (FIG. 1) so that the voltage $V_i$ representative of the maximum temperature of the temperature sensor 24 resulting from the heating thereof is sampled and stored in response to a logical one (1) state of output $T_f$.

Accordingly, as illustrated by comparing the waveforms shown in FIG. 3, sequencing and timing circuit 20 sequentially and periodically provides appropriate signals for sampling and storing ambient temperatures of the environment in proximity to the temperature sensor 24, for heating the temperature sensor 24, and for sampling and storing maximum temperatures of the temperature sensor 24 due to the heating during each 60 second cycle of operation of the apparatus 10.

Figure 4:
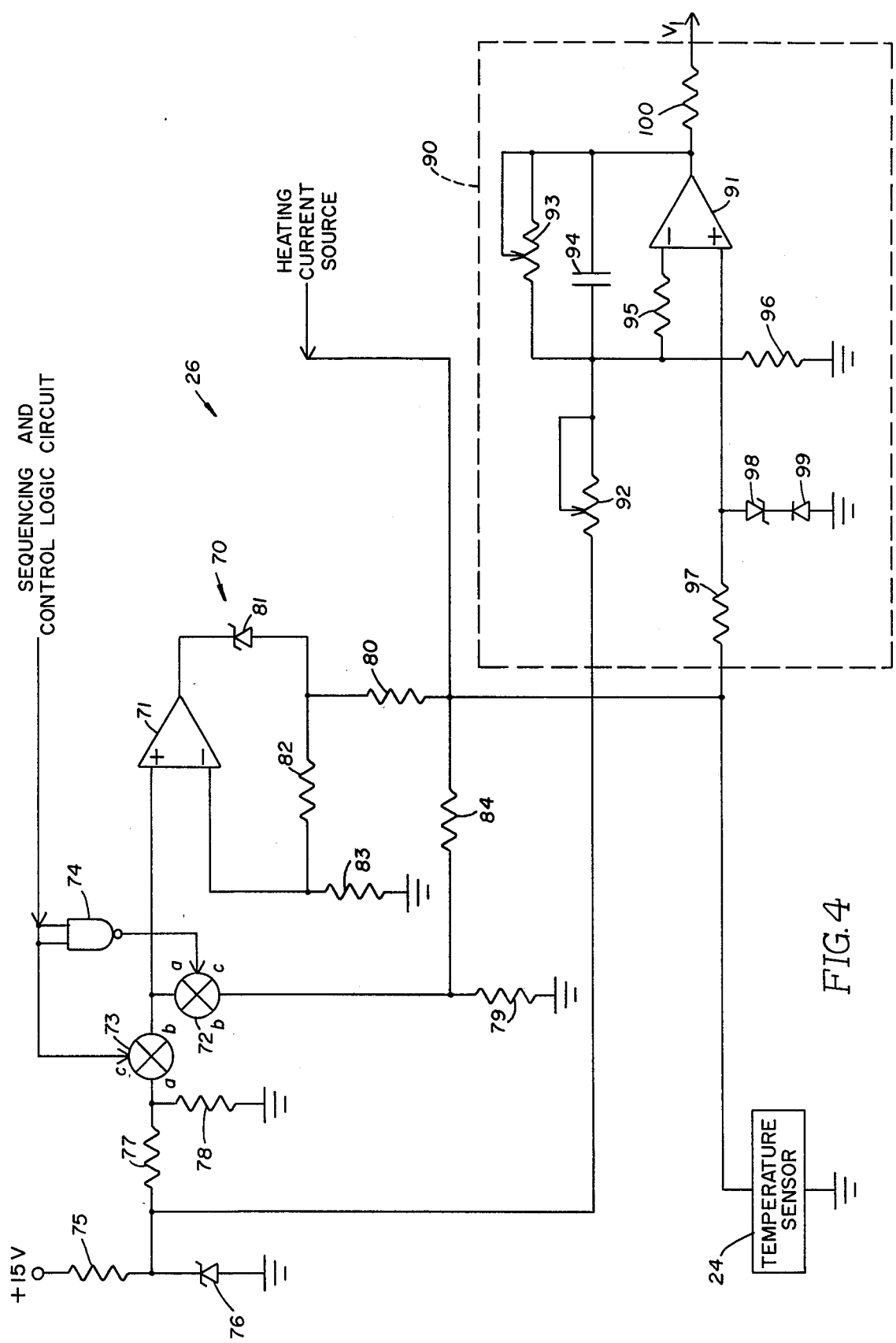
FIG. 4 is a schematic circuit diagram of an embodiment of a functional section of the apparatus shown in FIG. 1.

Referring now to FIG. 4, a preferred embodiment of biasing and temperature measuring circuit 26 includes circuit means 70 for forward biasing the temperature sensor 24 (zener diode) during temperature sensing and for reverse biasing the temperature sensor 24 (zener diode) during the heating thereof and circuit means 90 for detecting and measuring the temperatures sensed by temperature sensor 24. It should be noted that if other temperature sensors are used e.g. an ordinary diode or a thermistor, biasing circuit means 70 is unnecessary and therefore may be removed. Circuit means 70 is responsive to the output H of NAND gate 64 of sequencing circuit 62 and includes an operational amplifier 71, which may for example be of the LM 741 series manufactured by National Semiconductor Corporation, having its positive (+) input responsive to the states of two transmission gates 72 and 73. The opened or closed states of transmission gate 72 are determined by the state of a two-input NAND gate 74. Each of the inputs of NAND gate 74 are electrically coupled to and therefore responsive to the output H of NAND gate 64 of sequencing circuit 62 so that when the output H of NAND gate 64 is a logical zero (0) transmission gate 72 is closed and when the output H of gate 64 is a logical one (1) transmission gate 72 is opened. The opened and closed states of transmission gate 73 are determined by the output H of NAND gate 64 so that when the output H of NAND gate 64 is a logical zero (0) transmission gate 73 is opened and when the output H is a logical one (1) gate 73 is closed. As previously described, heating source 22 is activated in response to a logical zero (0) state of output H and remains deactivated in response to a logical one (1) state of output H. Accordingly, it can be seen that transmission gate 72 is closed during heating and open during temperature sensing whereas gate 73 is closed during temperature sensing and opened during heating.

One terminal of a transmission gate 73 is electrically coupled to a 15 volt power supply which has been reduced to a 1.2 volt reference voltage by the combination of resistor 75, zener diode 76, and a voltage divider network including resistors 77 and 78. The other terminal b of gate 73 is electrically coupled to the positive (+) input of amplifier 71.

One terminal b of transmission gate 72 is electrically coupled to a voltage divider network including resistors 79 and 84 which provides a 4 volt reference voltage. The other terminal of a gate 72 is also electrically coupled to the positive (+) input of amplifier 71.

The negative (−) input of amplifier 71 is electrically coupled to and therefore responsive to the voltage of a voltage divider network including resistors 82 and 83 which provides a 4 volt reference voltage to the negative (−) input amplifier 71.

The output of amplifier 71 is electrically coupled through a resistor 80 and zener diode 81 to the temperature sensor 24. By biasing the temperature sensor 24 (zener diode) through resistor 80 the current passing through the temperature sensor 24 substantially equals the temperature of the temperature sensor 24.

In the preferred embodiment of temperature sensor 24, a 20 volt zener diode is used having a 1.2 volt forward biased voltage. During temperature sensing by temperature sensor 24, transmission gate 73 is closed providing the necessary 1.2 reference voltage to forward bias the temperature sensor 24 (zener diode). When a signal is provided by the output H of gate 64 of sequencing circuit 62 to heat temperature sensor 24, transmission gate 72 is closed whereby 4 volts appears at both the positive (+) and (−) inputs of amplifier 71. Accordingly, temperature sensor 24 is reversed biased and resistor 80 is biased so that the voltage at both of its ends is 20 volts. Accordingly, no current flows through resistor 80. Zener diode 81 serves to provide a sufficient drop in the 20 volts across temperature sensor 24 that the sensor 24 is operable within the voltage range of amplifier 71. Since the current heating source 22 operates at a constant voltage, the increase in current through temperature sensor 24 is indicative of the temperature of the sensor 24.

Circuit means 90 for measuring and detecting the temperature sensor 24 is operable within the voltage range of amplifier 71. Since the current heating source 22 operates at a constant voltage, the increase in current through temperature sensor 24 is indicative of the temperature of the sensor 24.

Circuit means 90 for measuring and detecting the temperature of sensor 24 monitors the voltage across sensor (zener diode) 24. The voltage of the sensor 24 decreases linearly as the current/temperature increases. Circuit means 90 includes an operational amplifier 91 which may be of the LM 747 series manufactured by National Semiconductor Corporation. Resistors 92, 93, 95, 96 and 100 and capacitor 94 are electrically coupled to amplifier 91 in a conventional manner and in combination with amplifier 91 provide an output voltage $V_1$ proportional to the change in the voltage (temperature) across the sensor (zener diode) 24. The output voltage $V_1$ has a range of ±4 volts. It should be noted that 92 and 93 are variable for calibration purposes; however, it will be understood that resistors having fixed resistance values could be substituted therefor without a substantial effect on the operation. Resistor 97, zener diode 98, and diode 99 are interposed in the manner illustrated in FIG. 4 between the positive (+) input of the operation amplifier 91 and the temperature sensor 24 to preclude application of the full 20 volts associated with sensor (zener diode) 24 to the positive (+) input of the amplifier 91 during the heating of the sensor 24.

Figure 5:
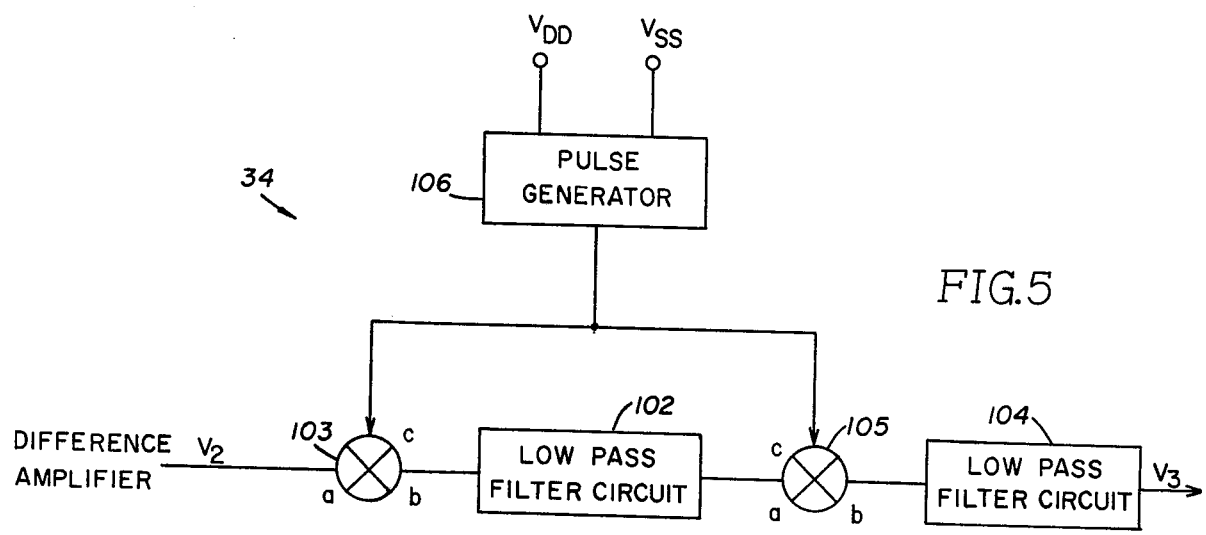
FIG. 5 is a schematic circuit diagram of an embodiment of a functional section of the apparatus shown in FIG. 1.

Referring now to FIG. 5, the output voltage $V_2$ of the difference amplifier may be represented by the equation:

$$V_2 = V_f - V_i = K(\Delta T)$$

where $\Delta T = T_f - T_i$ $K =$ A constant representing the proportionale relationship between the output voltages $V_1$ of circuit means 90 and the temperature T of the sensor 24.

In order to assure that a false indication of the presence or absence of a material on the liquid surface is not detected, the output voltages $V_2$ of the difference amplifier 32 are filtered and time averaged to compensate for spurious increases or decreases in the voltage $V_2$. A circuit means 34 provides a system 10 output $V_3 = \overline{(V_2(t))}$ and includes two conventional low pass filter circuits 102 and 104 each having associated therewith a a logical one (1) applied to their digital inputs c allow circuits 102 and 104 to sample voltages $V_2$ and hold such voltages for a period of time. It should be noted that if gates 103 and 105 where closed continuously, circuit 34 would serve as a low pass filter and time average the output voltage $V_2$ of difference amplifier 32 over a given time period. A pulse generator 106 periodically provides a signal to intermittently close gates 103 and 105 thereby allowing circuits 102 and 104 to time average over a longer period of time and filter the output voltage $V_2$ of difference amplifier 32. Pulse generator 106 may be any conventional squarewave oscillator which periodically provides an electrical pulse appropriate to close gates 103 and 105.

The resulting output voltage $V_3$ of the apparatus 10 (FIG. 1) may be compared with preset threshold levels of a conventional detection circuit (not shown) such that when an increase or decrease in the output voltage $V_3$ occurs, the detection circuit indicates by visual or audible means the presence or absence of a material on the liquid surface or the total submersion of the sensor 24 in the liquid.

What is claimed is:

1. Apparatus for detecting the presence of a substance on a liquid surface comprising: a semiconductor sensing element adapted to be at least partially immersed in said liquid having a thermal resistance related to its proximal environment; a heating source coupled to said sensing element for temporarily heating said element; temperature measuring means responsive to an electrical property of said sensing element; and control logic for sequentially sampling measured ambient temperatures of said proximal environment, temporarily heating said sensing element, sampling measured peak temperatures resulting from temporarily heating said sensing element, and differentiating between said measured ambient temperatures sampled prior to heating said sensing element and said measured peak temperatures whereby said apparatus is not susceptible to ambient temperature fluctuations.

2. The apparatus as recited in claim 1 wherein said thermal resistance of said sensing element is inversely related to thermal conductivity of said proximal environment.

3. The apparatus as recited in claim 2 wherein said sensing element is a diode situated in proximity to said liquid.

4. The apparatus as recited in claim 3 wherein said sensing element is a zener diode biased in a forward direction for sensing and biased in a reverse direction for heating.

5. The apparatus as recited in claim 1 wherein said sensing element current is directly related to the temperature of said sensing element whereby said ambient and peak temperatures are measured by said measuring means in response to said sensing element current.

6. The apparatus as recited in claim 5 wherein said heating source is a constant current source and said sensing element is heated by passing an electrical current therethrough.

7. The apparatus as recited in claim 6 wherein said thermal resistance of said sensing element changes in response to a change in thermal conductivity of said proximal environment thereby causing a corresponding change in said peak temperatures of said sensing element.

8. The apparatus as recited in claim 6 wherein said thermal resistance of said sensing element increases in response to a decrease in thermal conductivity of said proximal environment due to the presence of said substance thereby causing a corresponding increase in said peak temperatures of said sensing element.

9. The apparatus as recited in claim 1 further including circuit means for biasing said sensing element.

10. The apparatus as recited in claim 9 wherein said sensing element is a zener diode and said biasing means biases said zener diode in a forward direction for sensing and in a reverse direction for heating.

11. The apparatus as recited in claim 1 wherein said control logic includes means for continuously sequencing and timing the operation of said apparatus having a plurality of outputs, said heating source being activated and deactivated in response to logical states of at least one of said outputs.

12. The apparatus as recited in claim 11 wherein said control logic further includes means for sampling and storing a measured ambient temperature of said proximal environment prior to activation of said heating source, said ambient temperature sampling and storing means being activated and deactivated in response to logical states of at least one of said outputs.

13. The apparatus as recited in claim 12 wherein said control logic further includes means for sampling and storing a measured peak temperature of said sensing element resulting from applying a constant heating current thereto, said peak temperature sampling and storing means being activated and deactivated in response to logical state of at least one of said outputs.

14. The apparatus as recited in claim 13 wherein said peak temperature of said sensing element is related to said thermal resistance of said sensing element whereby a change in said thermal resistance results in a corresponding change in said peak temperature.

15. The apparatus as recited in claim 14 wherein said control logic further includes means for differentiating between a stored ambient temperature and a stored peak temperature.

16. The apparatus as recited in claim 15 wherein a change in the difference between said measured ambient temperatures and said measured peak temperatures is indicative of a change in thermal resistance of said sensing element, said thermal resistance being inversely related to thermal conductivity of said proximal whereby a change in thermal conductivity of said proximal environment is indicated as the presence of said substance.

17. A method of detecting the presence of a substance on a liquid surface comprising the steps of: storing ambient temperature sensed by a temperature sensing element situated at said liquid surface, subsequently heating said temperature sensing element by applying heating power thereto for a predetermined period of time, storing peak temperatures of said sensing element resulting from said heating, differentiating between said ambient temperatures and said peak temperatures, and detecting a change in difference between said temperatures.

18. The method as recited in claim 17 further including the step of sensing said ambient temperatures and said peak temperatures by measuring an electrical characteristic of said sensing element.

19. The method as recited in claim 18 wherein periodically an ambient temperature is sensed, said sensing element is heated, a peak temperature is sensed, and said ambient temperature and said peak temperature are differentiated.

20. The method as recited in claim 19 wherein said step of heating includes passing an constant electric current through said sensing element for said predetermined period of time.

21. The method as recited in claim 20 further including the step of biasing said temperature sensing element in a forward direction for sensing and biasing said temperature sensing element in a reverse direction for heating.

22. The method as recited in claim 17 further including the step of sequentially activating means for storing said ambient temperatures and said peak temperatures and means for heating said sensing element for predetermined periods of time.

23. The method as recited in claim 22 further including the step of subsequent to the step of differentiating between said ambient temperatures and said peak temperatures, averaging a plurality of differentials over a period of time whereby false indications due to spurious changes in difference between said temperatures are minimized.

* * * * *